US 11,707,188 B2

(12) United States Patent
Gilkey et al.

(10) Patent No.: US 11,707,188 B2
(45) Date of Patent: *Jul. 25, 2023

(54) IMAGING ELEMENT CLEANING APPARATUS WITH STRUCTURE-MANDATED CLEANING MEMBER MOTION CONTROL

(71) Applicant: ClearCam Inc., Austin, TX (US)

(72) Inventors: James Landon Gilkey, Dripping Springs, TX (US); Mitchell Ross Gilkey, Austin, TX (US)

(73) Assignee: ClearCam Inc., Austin, TX (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/178,783

(22) Filed: Feb. 18, 2021

(65) Prior Publication Data
US 2021/0177250 A1   Jun. 17, 2021

Related U.S. Application Data

(63) Continuation of application No. 17/068,563, filed on Oct. 12, 2020, now Pat. No. 10,959,610, which is a (Continued)

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00066* (2013.01); *A61B 1/00087* (2013.01);
(Continued)

(58) Field of Classification Search
CPC .. A61B 1/126; A61B 1/00066; A61B 1/00135
See application file for complete search history.

(56) References Cited

U.S. PATENT DOCUMENTS 5,392,766 A   2/1995   Masterson et al.
5,518,502 A   5/1996   Kaplan et al.
(Continued)

FOREIGN PATENT DOCUMENTS

CN   101883531 B   7/2014
EP   0647425 A1   4/1995
(Continued)

OTHER PUBLICATIONS

International Search Authority, Notification of Transmittal of the International Search Report and Written Opinion of the International Search Authority, PCT/US2019/063369, 16 pages.

*Primary Examiner* — Matthew J Kasztejna
(74) *Attorney, Agent, or Firm* — David O. Simmons; IVC Patent Agency

(57) ABSTRACT

Embodiments of the present invention are directed to providing an effective and reliable approach for cleaning an exposed surface of an imaging element (e.g., a lens) of apparatuses including but not limited to medical imaging instruments such as endoscopes and laparoscopes and the like. In the case of medical imaging instruments, cleaning apparatuses configured in accordance with embodiments the present invention can be cleaned while the distal end portion of the endoscope is in vivo. Such apparatuses have a cleaning member incorporated therein (e.g., a resilient polymeric wiper, a sponge, an absorbent pad or the like) that is used for cleaning the exposed surface of the imaging element. The apparatus is preferably adapted for being mounted on the imaging apparatus but can also be entirely or partially integral with one or more components of the imaging apparatus or system of which it is a component.

24 Claims, 9 Drawing Sheets

Related U.S. Application Data continuation of application No. 16/593,204, filed on Oct. 4, 2019, now Pat. No. 11,284,789.

(51) Int. Cl.
*A61B 90/70* (2016.01)
*A61B 1/313* (2006.01)

(52) U.S. Cl.
CPC ........ *A61B 1/00135* (2013.01); *A61B 1/3132* (2013.01); *A61B 90/70* (2016.02); *A61B 2090/701* (2016.02); *A61M 2209/10* (2013.01)

(56) References Cited

U.S. PATENT DOCUMENTS

| | | |
|---|---|---|
| 6,755,782 B2 | 6/2004 | Ogawa |
| 6,923,759 B2 | 8/2005 | Kasahara et al. |
| 7,543,314 B2 | 6/2009 | Kadykowski |
| 7,959,561 B2 | 6/2011 | Akui et al. |
| 8,690,764 B2 | 4/2014 | Clark et al. |
| 8,979,738 B2 | 3/2015 | Hsu et al. |
| 9,486,129 B2 | 11/2016 | Rodriguez Sanjuan |
| 9,763,567 B2 | 9/2017 | O'Prey et al. |
| 2006/0199998 A1 | 9/2006 | Akui et al. |
| 2009/0229067 A1 | 9/2009 | Becker et al. |
| 2009/0250081 A1 | 10/2009 | Gordin et al. |
| 2012/0101338 A1 | 4/2012 | O'Prey et al. |
| 2014/0094650 A1 | 4/2014 | Schaning |
| 2017/0332893 A1 | 11/2017 | Irion et al. |
| 2017/0367571 A1 | 12/2017 | Nave |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2015031026 A | 2/2015 |
| JP | 5735908 B2 | 6/2015 |
| WO | 200912587 A2 | 10/2009 |
| WO | 2014034839 A1 | 3/2014 |
| WO | WO2017006684 | 12/2017 |

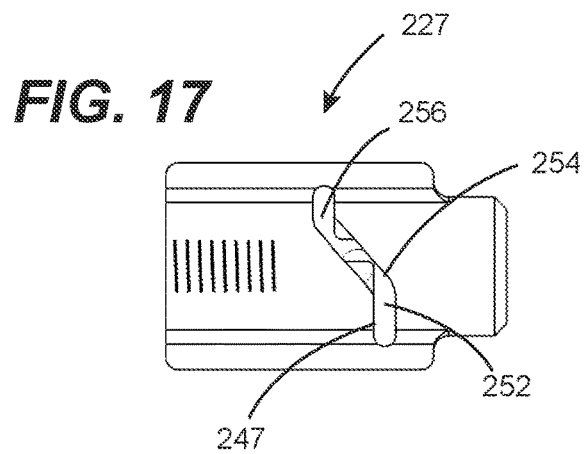
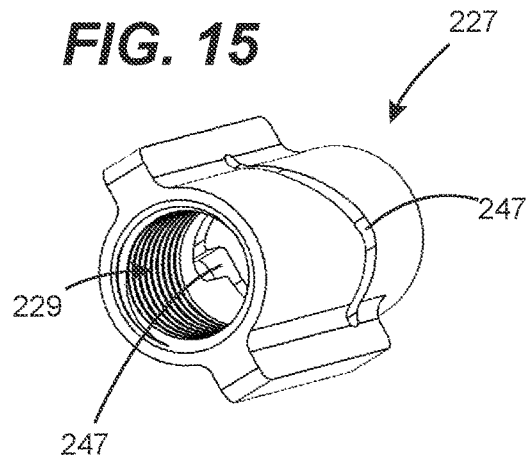
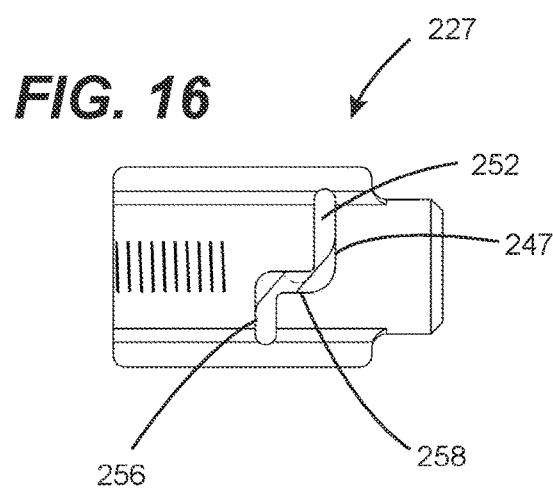
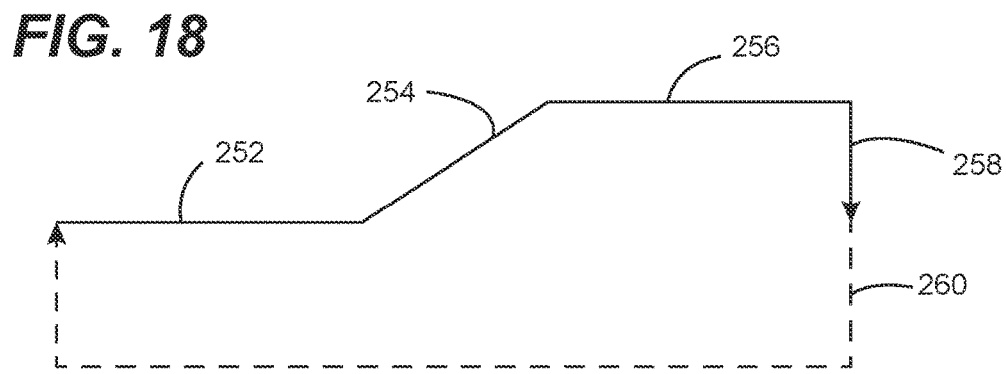

IMAGING ELEMENT CLEANING APPARATUS WITH STRUCTURE-MANDATED CLEANING MEMBER MOTION CONTROL

CROSS-REFERENCE TO RELATED APPLICATIONS

This patent application claims priority as a continuation from co-pending U.S. Non-Provisional patent application having Ser. No. 17/068,563, filed Oct. 12 2020, entitled "IMAGING ELEMENT CLEANING APPARATUS WITH STRUCTURE-MANDATED CLEANING MEMBER MOTION CONTROL", which claims priority as a continuation from co-pending U.S. Non-Provisional patent application having Ser. No. 16/593,204, filed Oct. 4, 2019, entitled "IMAGING ELEMENT CLEANING APPARATUS WITH STRUCTURE-MANDATED CLEANING MEMBER MOTION CONTROL", both of which have a common applicant herewith and are being incorporated herein in their entirety by reference.

BACKGROUND

Surgical procedures utilizing in vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization device for providing in vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

As shown in FIG. 1, an endoscope 1 used in these surgical procedures is characterized as having a user interface portion 5 and an extension portion 10 connected at its proximate end 15 to the user interface portion 5. Scopes for endoscopic surgery generally have an extension portion that is substantially flexible, whereas scopes for other types of surgical procedures—e.g., for laparoscopic surgery, as shown in FIG. 1—generally have an extension portion 10 that is substantially rigid. The extension portion 10 has an imaging element 20 such as a lens at its distal end portion 25. The imaging element 20 can have an exposed surface that is typically generally flush with or that defines an end face of the extension portion 10. The imaging element 20 is connected to an optical fiber or other image transmitting element that is internal to the endoscope. The optical fiber or other image transmitting element extends along the length of the extension portion 10 and terminates at an optics connector 30 on the user interface portion 5. The optics connector 30 enables the optical fiber to be connected to a visualization device (e.g., visual display console) through which target surgical sites can be viewed by surgery personnel.

During a surgical procedure using an endoscope, the exposed surface of the imaging element thereof may become impaired due to one or more in vivo scenarios. Examples of these scenarios include the exposed surface of the imaging element becoming fogged with moisture within the surgical space, or the exposed surface of the imaging element may be smeared by blood or other bodily fluids or tissues (e.g. interstitial fluid, fat tissue or the like). Currently, there are two primary different endoscope cleaning methods that are commonly utilized. The first of these cleaning methods is to remove the endoscope from the body, wipe the imaging element clean, and reinsert the endoscope into the body. This method, though effective, is time consuming and causes the surgeon to lose visual of the surgical site, which can be considered dangerous (e.g., risk of infection), as surgical instruments typically remain inside the body. The second of these cleaning methods is to wipe the exposed surface of the imaging element upon a nearby organ or tissue. Although the endoscope remains inside the body, takes less time to clean and does not potentially compromise the surgical site, this method is often not sufficiently effective either due to the "cleaning" surface not providing effective cleaning performance or simply further contaminating the exposed surface of the imaging element. Also, when using either of these cleaning methods, the surgeon must undesirably spend time relocating the surgical site after cleaning the imaging element.

At a minimum, current approaches for cleaning the exposed surface of the imaging element can be a hindrance and an annoyance for surgeons and may offer poor cleaning performance. Additionally, the action of cleaning the exposed surface of the imaging element increases the length of time a surgical procedure takes, thereby decreasing the amount of operating room (OR) time available to the hospital. It is also costly for hospitals, patients, and insurance companies due to wasted time, and possibly surgical complications and post-surgical infection rates. Additionally, as patients undergo longer procedures, their time spent under anesthesia increases. Increased time under anesthesia has been shown to correlate to a rise in surgical complication rates and post-surgical infection rates. Thus, the added time associated with current commonly used approaches for cleaning the exposed surface of the imaging element is not only a hindrance, but also potentially medically and financially costly.

Thus, to maintain required visualization of target surgical sites, it is desirable to clean an exposed surface of an imaging element of a device while the distal end portion of the device remains in a concealed operation site (e.g., an endoscope in vivo). Known methods and devices that are intended to provide for cleaning of a surface of such devices when still within the concealed operation site (e.g., an endoscope in vivo) have one or more shortcomings (e.g., lack efficacy, interfere with the surgical procedure, require significant alteration to a surgeon's preferred surgical technique, etc.). Therefore, an effective, efficient, simple and reliable approach for allowing an exposed surface of an imaging element of device (e.g., an endoscope) to be cleaned while the distal end portion of apparatus is still within the concealed operation site (e.g., in vivo) would be advantageous, desirable and useful.

SUMMARY OF THE DISCLOSURE

Embodiments of the present invention are directed to providing an effective and reliable approach for allowing an exposed surface of an imaging element (e.g., a lens) of a device (e.g., an endoscope) be cleaned while the distal end portion of the device is within a concealed operational site (e.g., in vivo). More specifically, one or more embodiments of the present invention provide an apparatus for use with an endoscope utilized in one or more types of surgical procedures (e.g., endoscopic surgery, laparoscopic surgery, thoracoscopic surgery and the like), The apparatus incorporates a cleaning member (e.g., a resilient polymeric wiper, a sponge, an absorbent pad or the like) used for cleaning the exposed surface of the imaging element of the device while the imaging element is within the concealed operation site. The apparatus is preferably adapted for having the device mounted thereon but can also be can be entirely or partially integral with one or more components of the device (e.g., a robotic arm configured for carrying, operating and manipulating an endoscope).

Cleaning apparatuses in accordance with one or more embodiments of the present invention can be configured to be used with commercially available endoscopes. Dimensions of such endoscopes are either published or otherwise publicly determinable. As a result of knowing the dimensions of the target endoscopes intended for use with a cleaning apparatus in accordance with one or more embodiments of the present, cleaning apparatuses configured in accordance with one or more embodiments of the present invention can be engineered device-specific. Thus, engagement of a device such as an endoscope on an intended one of these device-specific cleaning apparatuses preferably results in the device having a seated configuration on the cleaning apparatus exhibiting a high level of dimensional precision between the device and the cleaning apparatus.

Although such high level of dimensional precision is exhibited, both the device and the cleaning apparatus have respective manufacturing tolerances that can influence the efficiency, effectiveness and predictability by which the cleaning member cleans the imaging element. For example, in view of cleaning apparatuses configured in accordance with embodiments of the present invention relying upon contact with portions of the device comprising the imaging element (e.g., direct surface contact between the imaging element and the cleaning member), these manufacturing tolerances can influence a degree of force and/or deflection that the cleaning member exhibits as it comes into contact with the imaging element and thereby influence cleaning performance. Similarly, in some situations (e.g., rate of speed by which the cleaning member is brought into contact with the imaging element, direction of motion of the cleaning member and the like), other consideration can also influence the degree of force and/or deflection that the cleaning member exhibits as it comes into contact with the imaging element.

Advantageously, cleaning apparatuses configured in accordance with embodiments of the present invention can include a mechanism for selectively adjusting the axial position of the cleaning member—an axial position adjuster. The axial position of the cleaning member is relative to the distal end portion of the device (e.g., the distal end portion of the extension portion of the endoscope). In most instances, the axial position will be relative to a face of an imaging element exposed at an end face of the extension portion. Through such adjustment of the axial position of the cleaning member, a user can alter the degree of force and/or deflection that the cleaning member exhibits as it comes into contact with the end portion of the endoscope and/or imaging element, thereby optimizing cleaning functionality.

In one or more embodiments of the present invention, an in vivo endoscope cleaning apparatus comprises a chassis, a cleaning member and a cleaning member movement mechanism. The chassis is adapted for having an endoscope attached thereto. The cleaning member is provided at a distal end portion of the chassis. The cleaning member movement mechanism is provided at a proximate end portion of the chassis. The cleaning member movement mechanism includes a cleaning member movement assembly including a control body and a motion control device. The motion control device is attached to the control body and to the cleaning member. The motion control device includes a motion control structure that defines an axial position of the cleaning member as a function of angular position of the control body.

In one or more embodiments of the present invention, an in vivo endoscope cleaning apparatus comprises a chassis, a coupling element, and a cleaning member movement mechanism. The chassis is adapted for having an endoscope attached thereto a cleaning member at a location of the chassis that is adjacent to an imaging element of the endoscope when the endoscope is mounted on the chassis. The coupling element has a distal end thereof attached to the cleaning member. The cleaning member movement mechanism includes a cam body, a control body and a cleaning member coupling element. The cam body is engaged with the chassis and includes a motion control surface having a profile that defines axial movement of the cleaning member coupling element with respect to the cam body as a function of angular position of the control body. The control body is attached to the cleaning member coupling element whereby rotation of the control body causes a corresponding rotational movement of the cleaning member coupling element. The cleaning member coupling element is translatably and rotatably engaged with the cam body and has a proximate end of the coupling element fixedly attached thereto. At least one of the control body and the cleaning member coupling element has a motion coupling element thereof engaged with the motion control surface whereby rotation of the control body results in translational and rotational movement of the cleaning member relative to the elongated member in accordance with the profile of the motion control surface.

In one or more embodiments of the present invention, a cleaning member controller of an in vivo endoscope cleaning apparatus comprises a cleaning member coupling element, a control body and a cam body. The cleaning member coupling element is fixedly coupled to a cleaning member of the in vivo endoscope cleaning apparatus. The control body is attached to the cleaning member coupling element to provide for rotation of the control body to cause a corresponding rotational movement of the cleaning member coupling element. The cam body has a chassis engaging portion engaged with a chassis of the in vivo endoscope cleaning apparatus. The cam body includes a motion control surface having a profile that defines axial movement of the cleaning member coupling element with respect to the cam body as a function of angular position of the control body. The cleaning member coupling element is translatably and rotatably engaged with the cam body. The cleaning member coupling element has a motion coupling element thereof engaged with the motion control surface whereby rotation of the control body results in translational and rotational movement of the cleaning member relative to the elongated member in accordance with the profile of the motion control surface.

It is an object of one or more embodiments of the present invention to provide a camming device that synchronously controls movement of the cleaning member.

It is an object of one or more embodiments of the present invention for a motion control surface of the camming device to define a circuitous path that defines such synchronous movement control.

It is an object of one or more embodiments of the present invention that such synchronous movement control causes the wiper to move from a stowed position to a use position back to the stowed position.

It is an object of one or more embodiments of the present invention that such synchronous movement control can be implemented by manipulation of a single control body.

It is an object of one or more embodiments of the present invention that the camming device that at least partially limits a direction in which the single control body can be moved.

It is an object of one or more embodiments of the present invention to provide a plurality of control bodies where at least one of the control bodies is in a nested arrangement with respect to at least one of the one of the control bodies.

It is an object of one or more embodiments of the present invention to provide a cleaning member that is at least one of a resilient wiper, a semi-rigid wiper, an absorbent pad and a sponge.

It is an object of one or more embodiments of the present invention to provide a single control mechanism that provides for multiple modes of cleaning member movement.

It is an object of one or more embodiments of the present invention to provide for selective adjustment of the axial position of the cleaning member.

It is an object of one or more embodiments of the present invention for such axial distance adjustability to be provided by a control device that is integral with the single control mechanism that provides for multiple modes of cleaning member movement.

These and other objects, embodiments, advantages and/or distinctions of the present invention will become readily apparent upon further review of the following specification, associated drawings and appended claims.

BRIEF DESCRIPTION OF THE DRAWINGS

FIG. 15 is a perspective view of a cam body of the cleaning apparatus shown in FIG. 13.

FIG. 16 is a first plan view of the cam body of FIG. 15.

FIG. 17 is a second plan view of the cam body of FIG. 15.

FIG. 18 is a diagrammatic view showing a profile of cam segments of the cam body of FIG. 15.

DETAILED DESCRIPTION

Figure 1:
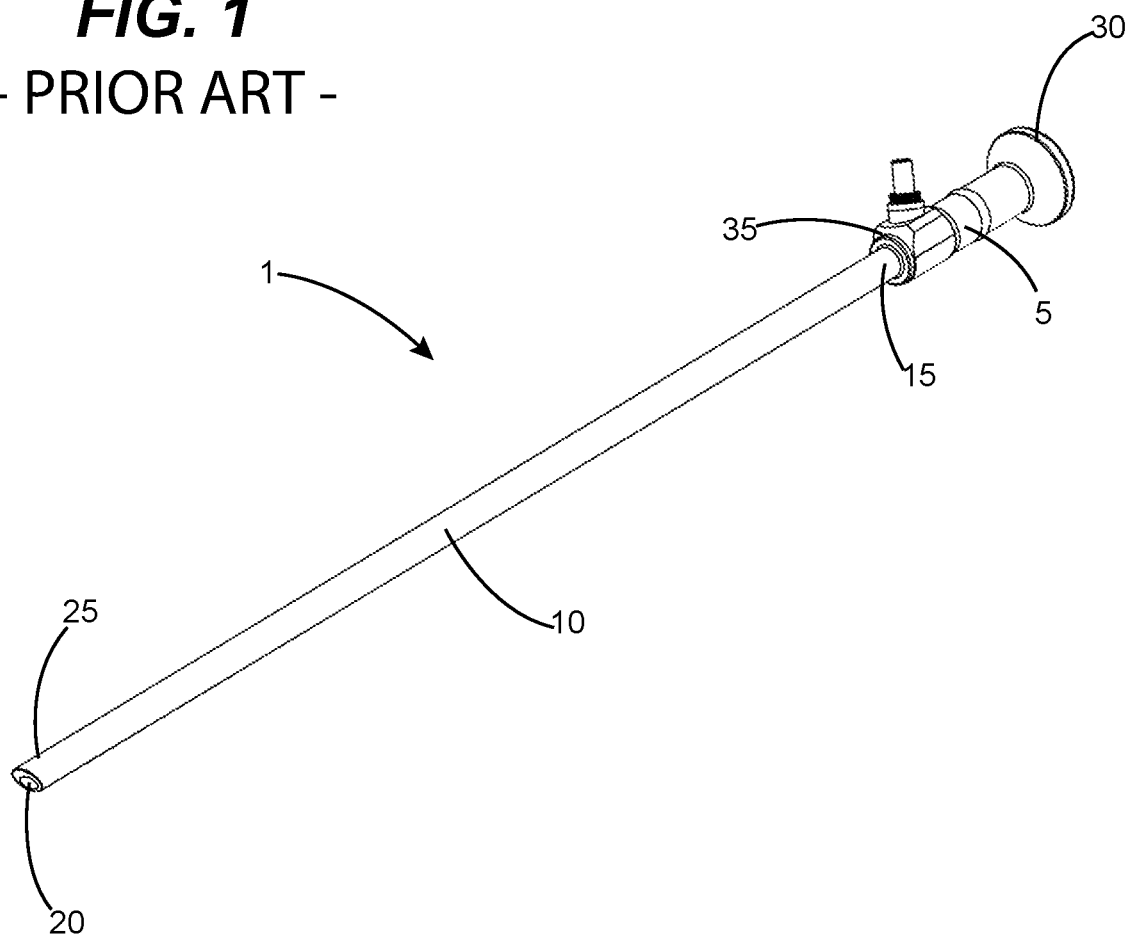
FIG. 1 is a perspective view showing a prior art endoscope.

FIGS. 2-10 illustrate various aspects of an in vivo endoscope cleaning apparatus configured in accordance with a first embodiment of the present invention, which is designated as cleaning apparatus 100. Cleaning apparatus 100 is preferably, but not necessarily, configured to be used with commercially available endoscopes, such as endoscope 1 of FIG. 1. Examples of such commercially available endoscopes include, but are not limited to, endoscopes manufactured under brand names of Karl Storz, Linvatec, Olympus, Richard Wolf, Stryker and Intuitive Surgical (i.e., DaVinci). To this end, in preferred embodiments, cleaning apparatus 100 can be engineered as endoscope-specific for a given model(s) of one or more manufacturers based on the dimensional attributes of such commercially available endoscopes. An underlying consideration of the manner in which the endoscope cleaning apparatus 100 is engineered for an intended brand(s) or model(s) of endoscope is that there be a high level of dimensional precision between the endoscope and the cleaning apparatus. Such dimensional precision can be characterized to include both the inhibition of any unacceptable level of relative movement between the endoscope and the cleaning apparatus 100 and relative placement of key structural elements of the endoscope relative to those of the cleaning apparatus 100.

Figure 2:
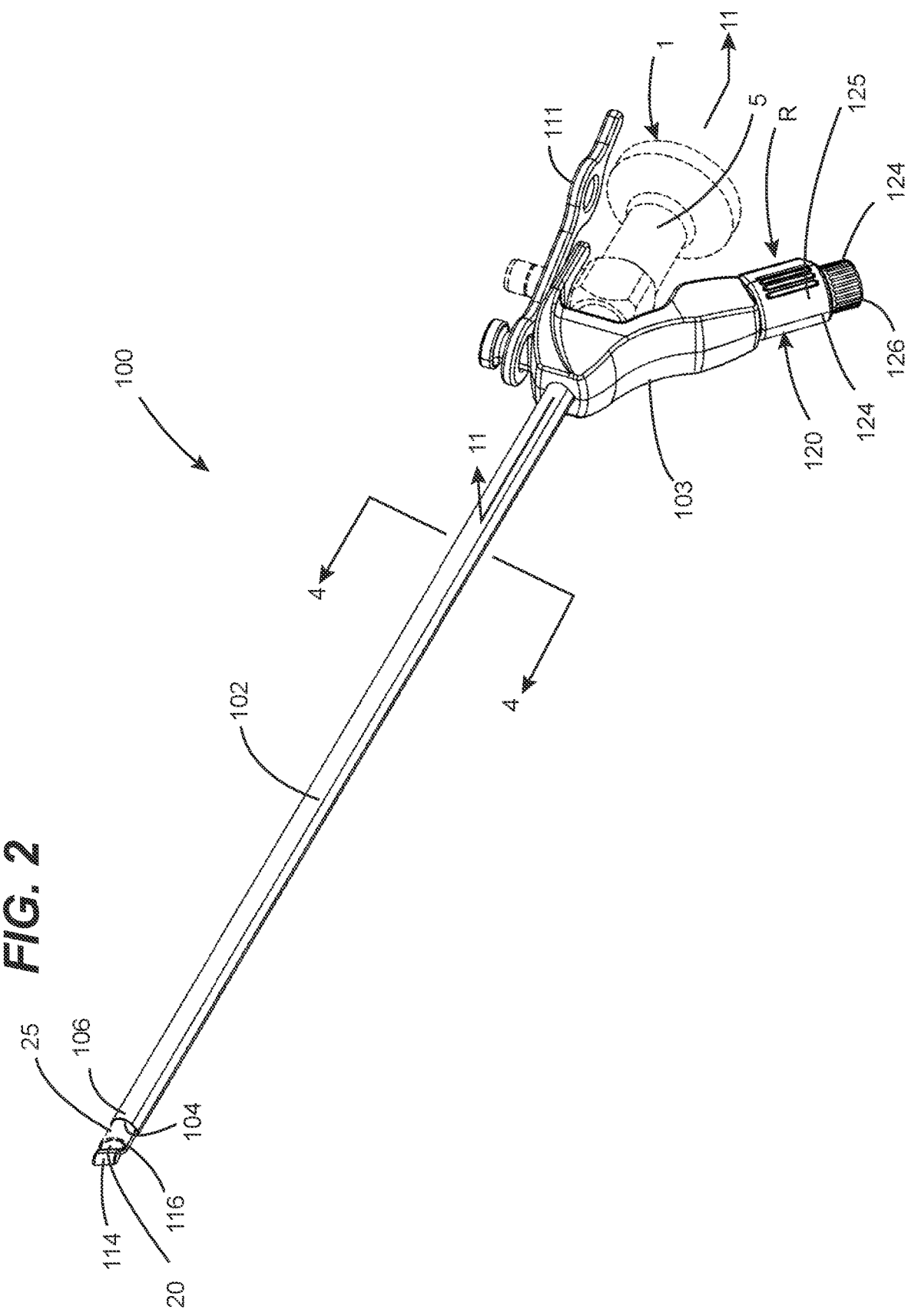
FIG. 2 is a first perspective view showing an endoscope cleaning apparatus in accordance with a first embodiment of the present invention.
Figure 3:
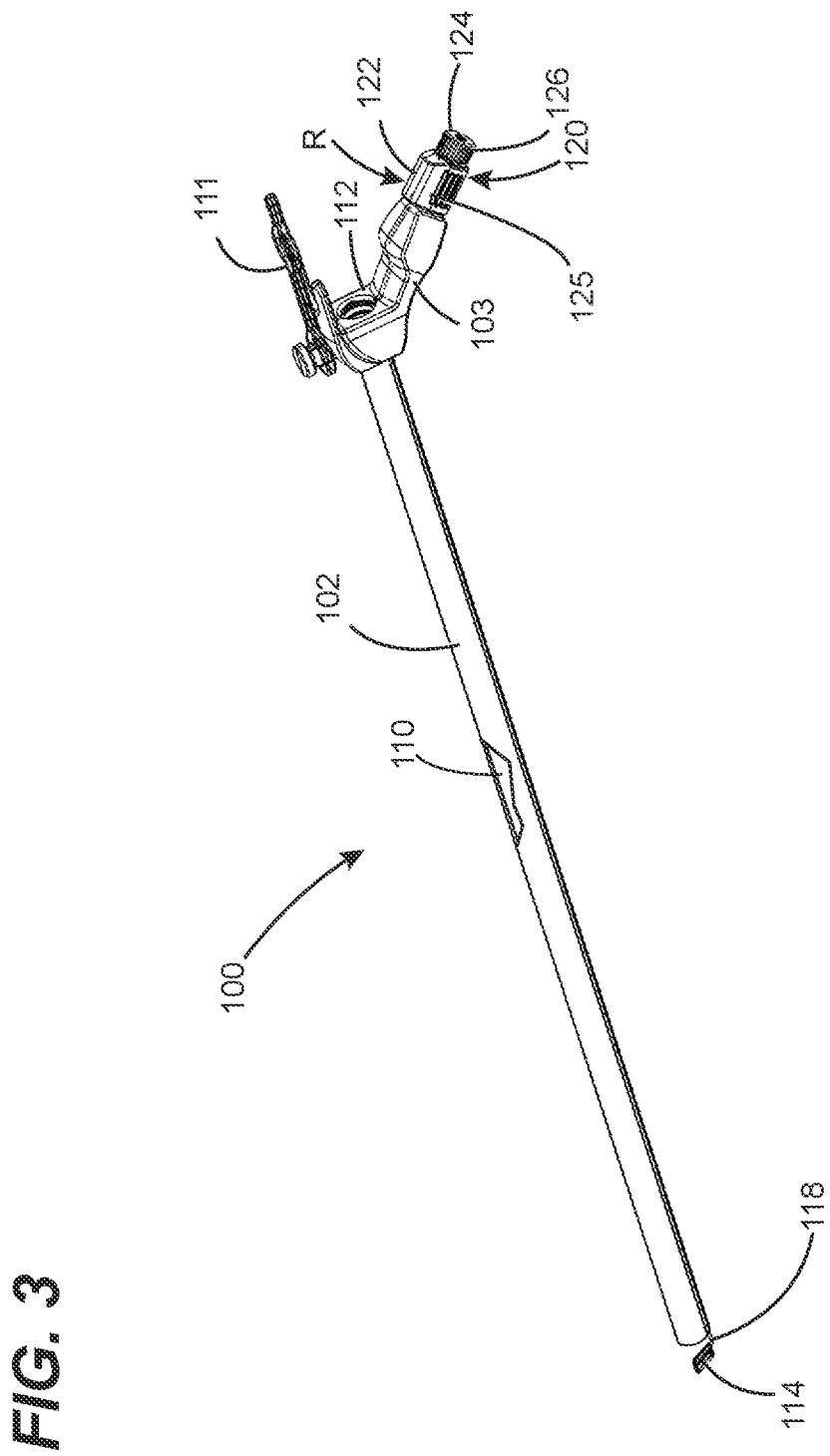
FIG. 3 is a second perspective view showing the endoscope of FIG. 2.

Still referring to FIG. 2, the cleaning apparatus 100 has an elongated body 102 that is adapted to have the extension portion 10 of the endoscope 1 inserted. In its fully seated placement, as shown, a dimensionally predictable surface or feature of the endoscope 1 such as that of the user interface portion 5 (e.g., a handle and/or optic interface portion) abuts a mating dimensionally predictable surface or feature of the endoscope cleaning apparatus 100. This mating surface or feature of the cleaning apparatus 100—such as a surface or feature of a user interface body 103 thereof—serves as a reference structure of the cleaning apparatus 100. With the endoscope 1 in this fully seated position on the cleaning apparatus 100 with respect to the reference structure, a distal end portion 25 of the endoscope protrude from within an opening 104 in the distal end portion 106 of the elongated body 102 by a known, predictable amount. Through such an interfacial arrangement and dimensional tolerances, a high level of dimensional precision between the endoscope 1 and the cleaning apparatus 100 can be achieved. As discussed below in greater detail, such dimensional precision is beneficial to the cleaning performance afforded by the cleaning apparatus 100.

As discussed above in reference to FIG. 1, the distal end portion 25 of the endoscope 1 carries the imaging element 20 (e.g., a lens). The imaging element 20 is exposed at and is generally flush with or defines an end face at the distal end portion 25 of the extension portion 10 of the endoscope 1. The distal end portion 25 of the endoscope 1 is exposed at an opening 104 in a distal end 106. As a result of the seated placement of the endoscope 1 on the cleaning apparatus 100, the imaging element 20 is at a known and predictable position relative to the reference structure of the cleaning apparatus 100. Thus, for an endoscope engineered for use with a specific cleaning apparatus, the components of the cleaning apparatus 100 can similarly be at known and predictable position relative to structures of the endoscope 1, thereby providing for precise placement and configuration of components of the cleaning apparatus 100 to achieve a desired and predictable level of cleaning performance.

Referring now to FIGS. 3-6, the elongated body 102 and the user interface body 103 jointly define a chassis of the cleaning apparatus. The chassis serves as the platform on which the endoscope 1 can be mounted in a predictable seated position. It is disclosed herein that the chassis can be that of a robot that provides robot-assisted surgery or can be adapted to operatively interface with a mating mounting portion of such a robot. For example, the elongated body 102 and/or the user interface body 103 can be that of an arm or other structure of the robot or adapted to operatively interface with an instrument mounting portion of the arm of the robot.

The elongated body 102 of the chassis can be a tube having a central passage 110 (shown in FIG. 3) with a round or generally round cross-sectional shape. The central passage 110 has a size and profile that is adapted to have the extension portion 10 of the endoscope 1 seated therein by inserting the extension portion into the central passage 110 and sliding the extension portion 10 along the length of the elongated body 102 until the endoscope 1 is in a seated position on the chassis. The user interface body 103 can include a retention tool 111 for securing the endoscope 1 is in the seated position on the chassis. Alternatively, the elongated body 102 can be a non-tubular structure such as a skeletal structure that engages the extension portion 10 of the endoscope at discrete spaced-apart locations thereof.

The chassis can include a plurality of structural elements that provide for the known and predictable position of the endoscope 1 when mounted in a seated position on the chassis. One of these structural elements is the effective inside diameter (e.g., for ribbed or textured interior surface) or the actual inside diameter (e.g., a smooth interior wall) of the elongated body 102 in relation to an outside diameter of the extension portion 10 of the endoscope 1 and the elongated body 102 of the chassis. It is preferable to maintain a close fit between the outside wall of elongated body 102 and the mating exterior wall of the extension portion 10 so as to provide for a fluid-resistant interface between the elongated body 102 and the extension portion 10 and to limit off-axis pitch between a longitudinal axis of the elongated body 102 and the extension portion 10. Another one of these structural elements is a seating surface 112 (shown in FIGS. 3 and 11) on the user interface body 103. The seating surface can be a reference surface of the cleaning apparatus 100 that engages a mating reference surface 35 (shown in FIG. 1) of the endoscope 1. Engagement of the seating surface 112 on the user interface body 103 with the mating reference surface 35 of the endoscope 1 serves to define a predictable seated orientation of the endoscope 1 on the chassis.

Figure 4:
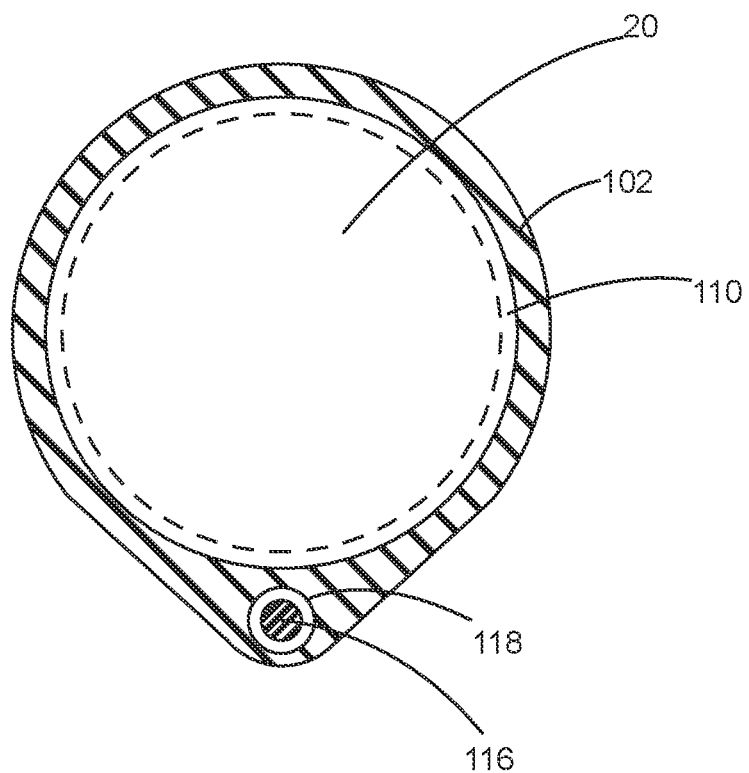
FIG. 4 is a cross-sectional view taken along the line 4-4 in FIG. 2.
Figure 10:
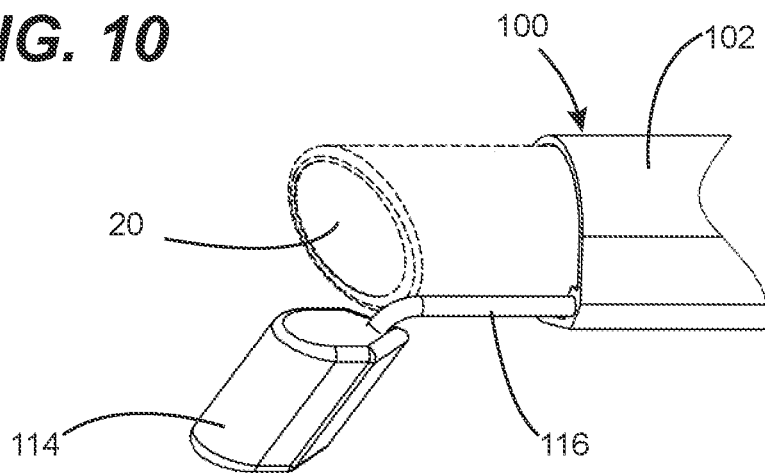
FIG. 10 is partial perspective view of the endoscope cleaning apparatus shown in FIG. 2, where the cleaning member thereof is moved beyond the imaging element contact position thereof.

The cleaning apparatus 100 includes a cleaning member 114 (shown in FIGS. 2 and 3) adjacent to the opening 104 in the distal end portion 106 of the elongated body 102. As discussed below in greater detail, the cleaning member 114 functions to clean contaminants and debris from a surface of the imaging element 20 when brought into contact with the imaging element 20 of the endoscope. The cleaning member 114 can be fixedly attached to a distal end portion of a coupling element 116. As best shown in FIG. 4, the coupling element 116 extends through a channel 118 within the elongated body 102. Preferably, the channel 118 and the central passage 110 extend substantially parallel to each other within the elongated body 102. In some embodiments, the coupling element 116 is characterized by an elongated small diameter structure that offers at least a limited degree of bendability in combination with high torsional rigidity. In other embodiments, the coupling element 116 is characterized by an elongated small diameter structure that offers a given amount of torsional compliance. Based on these characterizing attributes, examples of coupling element 116 include, but are not limited to, solid metallic wire, spiraled metal wire, a polymeric filament(s), a composite filament(s) or the like.

Figure 6:
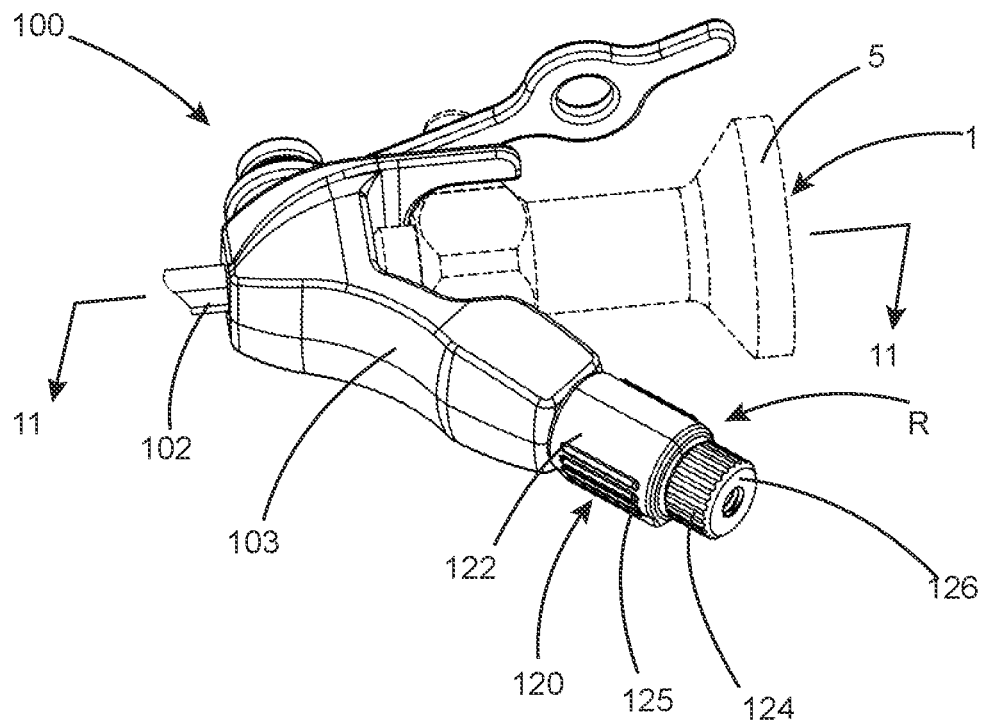
FIG. 6 is partial perspective view of the endoscope cleaning apparatus shown in FIG. 2, where a control body of a first cleaning member control mechanism is in a retracted configuration.
Figure 5:
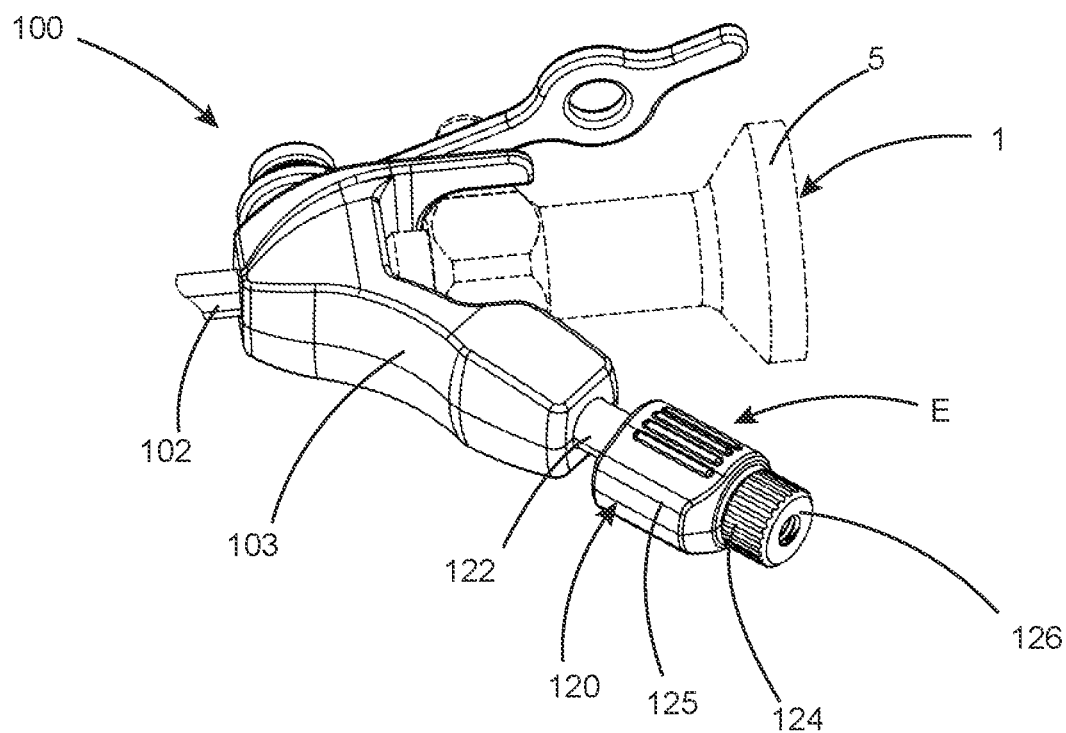
FIG. 5 is partial perspective view of the endoscope cleaning apparatus shown in FIG. 2, where a control body of a first cleaning member control mechanism is in an extended configuration.
Figure 7:
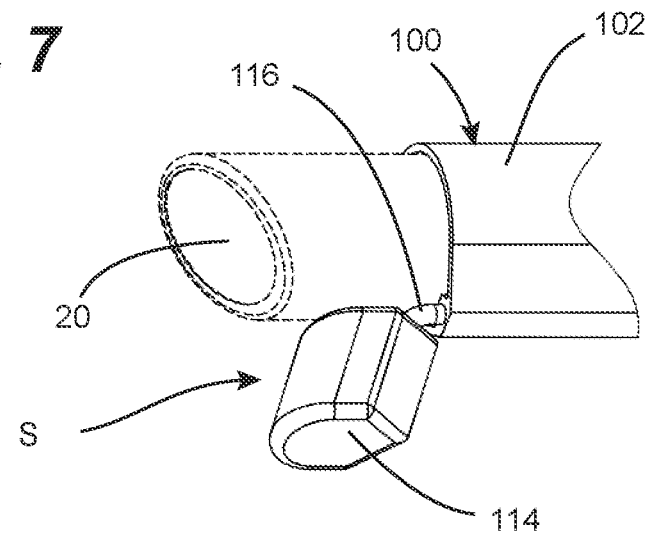
FIG. 7 is partial perspective view of the endoscope cleaning apparatus shown in FIG. 2, where a cleaning member thereof is in a stowed position.
Figure 8:
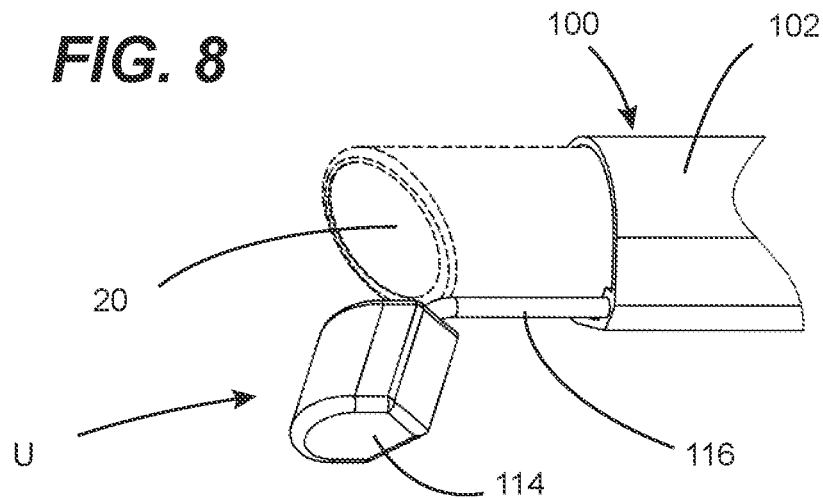
FIG. 8 is partial perspective view of the endoscope cleaning apparatus shown in FIG. 2, where the cleaning member thereof is in a use position.
Figure 9:
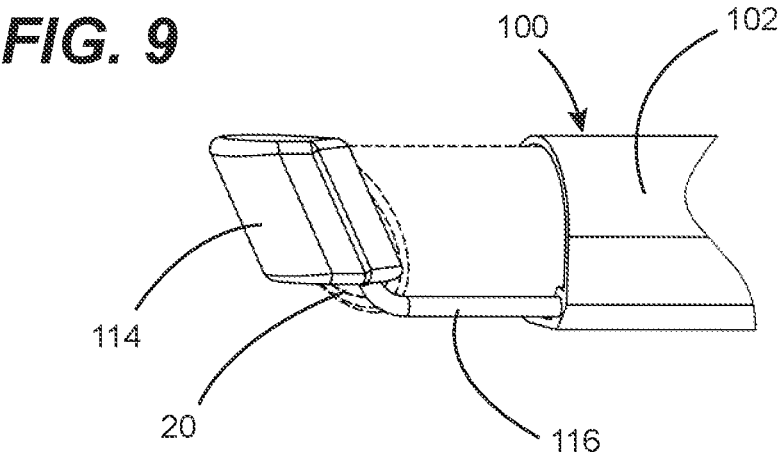
FIG. 9 is partial perspective view of the endoscope cleaning apparatus shown in FIG. 2, where the cleaning member thereof is moved to an imaging element contacting position thereof.

The user interface body 103, which can be configured as a handle for the cleaning apparatus 100, carries a cleaning member controller 120. The cleaning member controller 120 is coupled between the user interface body 103 and the cleaning member 114 for enabling selective movement of the cleaning member 114. The cleaning member controller 120 includes a first cleaning member control mechanism 122 (i.e., a cleaning member movement mechanism) and a second cleaning member control mechanism 124 (i.e., a cleaning member adjusting mechanism). The first cleaning member control mechanism 122 includes a control body 125 (i.e., the first control body 125) that is rotatably and translatably mounted on (i.e., attached to) the user interface body 103, as best shown in FIGS. 5 and 6 and the second cleaning member control mechanism 124 is rotatably mounted on the first cleaning member control mechanism 122. The first and second cleaning member control mechanisms 122, 124 provide for various cleaning member manipulation modes.

Through such movement capability of the first cleaning member control mechanism 122, the first cleaning member control mechanism provides at least a first cleaning member manipulation mode and a second cleaning member manipulation mode. The first cleaning member manipulation mode can include translational movement, as provided for by translation of the coupling element 116 to move the cleaning member 114 between a stowed position S (best shown in FIG. 7) and a use position U (best shown in FIG. 8)—i.e., the first cleaning member manipulation mode. As can be seen, the stowed position S and the use position U are relative to a location of the imaging element 20 of the endoscope 1 when the endoscope 1 is mounted on the chassis. As can be seen, the stowed position S and the use position U are relative to a location of the imaging element 20 of the endoscope 1 when the endoscope 1 is mounted on the chassis. The use position U is a position in which the cleaning element 114 is beyond a terminal end of the endoscope 1. The stowed position S is a position in which the cleaning element 114 is retracted from the use position U (e.g., by a maximum distance of travel therebetween). The second cleaning member manipulation mode can include rotational movement to move the cleaning member 114 into and away from contact with the imaging element 20 (as best shown in FIGS. 6 and 8-10) while the cleaning member 114 is in the use position—i.e., the second cleaning member manipulation mode or, as discussed below, an offset use position adjacent thereto. In this manner, the first cleaning member manipulation mode of the first cleaning member control mechanism 122 permits manipulation of the cleaning member 114 for enabling in vivo cleaning of the imaging element 20 in concert with in vivo surgical cavity visualization utilizing the imaging element 20.

As discussed above, the cleaning apparatus 114 and the endoscope 1 are jointly configured such that the imaging element 20 is at a known and predictable position relative to the reference structure of the chassis of the cleaning apparatus 100. Thus, due to dimensional properties of the endoscope 1 and the cleaning apparatus 100, the cleaning member 114 is at a known and predictable position relative to the imaging element 20. In at least one aspect, such known and predictable position of the cleaning member 114 relative to the imaging element 20 can be characterized as being an axial distance between a reference portion of the cleaning member 114 (e.g., edge portion of the cleaning member 114) and the exposed surface of the imaging element 20. This axial distance is a design parameter of the cleaning apparatus that enables the cleaning member 114 to remove (i.e., clean) debris and contaminants from the exposed surface of the imaging element 20 in response to the cleaning member 114 being moved into contact with (e.g., wiped across) the exposed face of the imaging element 20 during implementation of the second cleaning member manipulation mode when the cleaning member 114 is in the use position U.

Some situations can arise that influence the position of the cleaning member 114 relative to the imaging element 20 to a degree that can impair desired cleaning of the imaging element 20. One such situation is where dimension tolerances of the cleaning apparatus 114 and and/or the endoscope 1 result in a dimensional stack that influence the axial distance between the reference portion of the cleaning member 114 and the exposed surface of the imaging element 20 to a degree that adversely effects cleaning performance. For example, the extension portion 10 of the endoscope 1 can have a length that is at the lower end of its tolerance range and the mating reference surface 35 of the endoscope 1 can be at the upper end of its tolerance range. In this case, the axial distance between the reference portion of the cleaning member 114 and the exposed surface of the imaging element 20 can become greater than required for providing acceptable cleaning performance. Another such situation is where end user technique by which the user causes the cleaning member 114 to move across the imaging element 20 (e.g., the rate, cadence and/or rotation direction) can adversely influence cleaning performance.

Advantageously, cleaning apparatuses configured in accordance with one or more embodiments of the present invention include at least one provision for mitigating situations that can influence the position of the cleaning member 114 relative to the imaging element 20 to a degree that impairs desired cleaning of the imaging element 20. To this end, the second cleaning member control mechanism 124 provides a respective cleaning member manipulation mode—i.e., a third cleaning member manipulation mode— for selectively altering the axial distance between the reference portion of the cleaning member 114 and the exposed surface of the imaging element 20.

As shown in FIGS. 2, 3, 5 and 6, the second cleaning member control mechanism 124 includes a control body 126 that is rotatably (i.e., moveably) attached to the first cleaning member control mechanism 122 (i.e., the second control body). Through rotation of the second control body 126 in a given direction, a respective change in the axial distance between the reference portion of the cleaning member 114 and the exposed surface of the imaging element 20 occurs (e.g., clock-wise rotation provides lesser distance and counter clock-wise rotation provides greater distance or vice-versa). In this manner, an end user is able to alter the axial distance between the cleaning member 114 and the exposed surface of the imaging element 20 to affect cleaning member loading upon contact with the imaging element 20 and thus imaging element cleaning performance.

Figure 11:
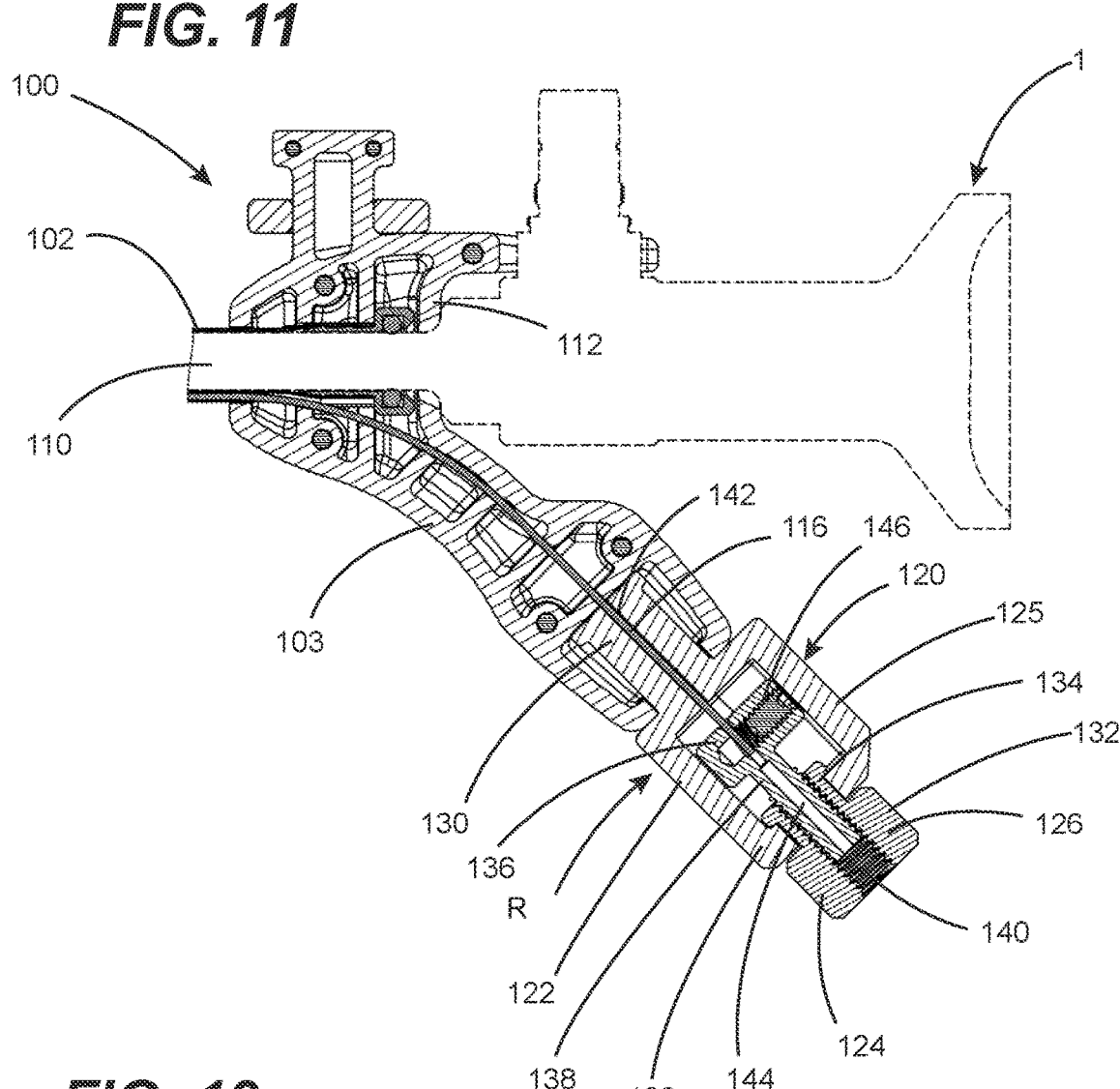
FIG. 11 is a cross-sectional view taken along the line 11-11 in FIG. 6.

Referring now, to FIG. 11, aspects of a specific implementation of the first and second cleaning member control mechanisms 122, 124 are described. The first control body 125 includes a user interface portion 128 and a mounting portion 130 connected to the user interface portion 128. The mounting portion 130 is translatably and rotatably attached to a mating portion of the user interface body 103. For example, the mounting portion 130 can include a cylindrical extension portion that is seated in a mating passage of the user interface body 103 to permit the first cleaning member control mechanism 122 to be axially translated relative to the user interface body 103 between an extended position E (FIG. 5) and a retracted position R (FIG. 6) for correspondingly moving the cleaning member 114 between the stowed position S and the use position U, and to be rotationally translated relative to the user interface body 103 for correspondingly moving the cleaning member 114 into and away from contact with the imaging element 20 of the endoscope 1. Dimensions of the mounting portion 130 and the mating passage of the user interface body 103 can jointly define the amount of translational movement that the cleaning member control mechanism 122 exhibits.

Still referring to FIG. 11, the second control body 126 includes a user interface portion 132 and a mounting portion 134 connected to the user interface portion 132. The mounting portion 134 is rotatably (i.e., movably) attached to a mating portion of the user interface portion 132 of the first cleaning member control mechanism 122 (e.g., the control body 125) for enabling rotation of the second control body 126 relative to the first control body 125 while inhibiting unrestricted axial translation therebetween (i.e., a rotation-enabling, translation-inhibiting interface). A coupling element engaging structure 136 of the second cleaning member control mechanism 124 is disposed on the first control body 125 so as to permit axial translation of the coupling element engaging structure 136 relative to the first cleaning member control mechanism 122 and to inhibit unrestricted rotational movement therebetween (i.e., a rotation-inhibiting, translation-enabling interface). For example, the coupling element engaging structure 136 can have an oblong lateral shape (e.g., rectangular) and be located within a mating elongated cavity of the first control body 125 that has an oblong lateral shape, thereby enabling relative axial translation of the coupling element engaging structure 136 and inhibit unrestricted relative rotational movement thereof.

An extension portion 138 of the coupling element engaging structure 136 (e.g., a first structural element of an interlocked interface structure) is threadedly engaged within a mating central passage 140 of the second control body 126 (e.g., a second structural element of an interlocked interface structure). Such threaded engagement is an example of interlocked engagement, whereby axial movement is a function of rotational movement. The mounting portion 130 of the first cleaning member control mechanism 122 has a coupling element passage 142 extending longitudinally therethrough and the coupling element engaging structure 136 has a coupling element passage 144 extending at least partially longitudinally therethrough. The mounting portion 130 of the first cleaning member control mechanism 122 and the coupling element engaging structure 136 are jointly configured such that the coupling element passages 142, 144 are longitudinally aligned. A proximate end portion of the coupling element 116 extends through the coupling element passage 142 of the first cleaning member control mechanism 122 into the coupling element passage 144 of the coupling element engaging structure 136. The coupling element engaging structure 136 includes a securement structure 146 (e.g., a threaded setscrew) for securing the coupling element 116 in a fixed placement relative to the coupling element engaging structure 136.

Through the treaded engagement between the extension portion 138 of the coupling element engaging structure 136 and the second control body 126, as discussed above, rotation of the second control body 126 relative to the first cleaning member control mechanism 122 causes axial translation of the coupling element engaging structure 136 relative to the first cleaning member control mechanism 122 and, thus, provides a corresponding axial displacement of the cleaning element 114 thereby adjusting the axial distance between the reference portion of the cleaning member 114 and the exposed surface of the imaging element 20 occurs (e.g., clock-wise rotation provides lesser distance and counter clock-wise rotation provides greater distance or vice-versa).

A user can use the cleaning member adjustment capability provided by the second cleaning member control mechanism 124 in any number of ways. For example, prior to a surgical procedure, a user can set-up an initial degree of contact between the cleaning element 114 and the imaging using such cleaning member adjustment capability. After mounting an endoscope on a chassis of the cleaning apparatus, the user can adjust the axial distance between the cleaning member 114 and the imaging element 20 such that the is no contact between the cleaning member 114 as the cleaning member 114 passes across the exposed surface of the imaging element 20. Using the cleaning member adjustment capability provided by the second cleaning member control mechanism 124, the user can then bring the cleaning element 114 into first contact with the imaging element 20 and then apply a given degree of "preload" to the cleaning member through use of the cleaning member adjustment capability. The cleaning member adjustment capability can also be utilized during the surgical procedure to further adjust the cleaning member axial distance (i.e., a greater or lesser contact loading on the cleaning member 114) to influence cleaning performance.

Figure 12:
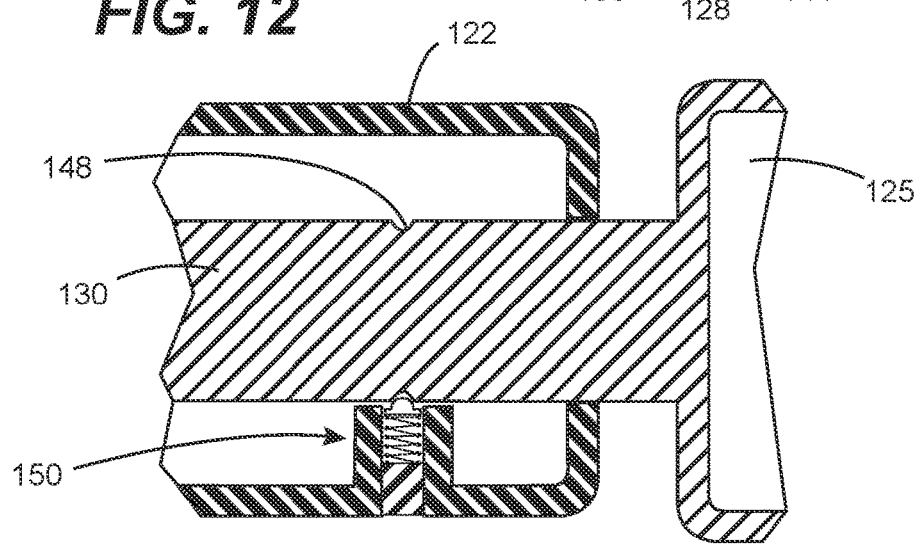
FIG. 12 is a partial cross-sectional view showing a structural arrangement for providing cleaning member offset functionality in accordance with one or more embodiments of the present invention.

One or more embodiments of the present invention can provide a cleaning member offset functionality. FIG. 12 illustrates an implementation of such cleaning member offset functionality provided for by the cleaning apparatus of FIGS. 2-11. Such cleaning member offset functionality serves to enable the position of the cleaning member 114 be precisely offset from its use position when the first control body 125 is in the retraced position R (See FIGS. 2, 3 and 6) at the limit of its retraction travel (i.e., fully retracted). To this end, a circumferential groove 148 can be provided in the mounting portion 130 of the first cleaning member control mechanism 122 corresponding to a desired offset location. The user interface body 103 includes a displacement controlling structure 150 that tactically and, optionally, audibly indicates when the first control body 125 has been translated from the retracted position R to the location defined by the location of the circumferential groove 148. A lateral distance between the groove 148 and the displacement controlling structure defines the offset distance of the cleaning member 114. In one or more embodiments, the displacement controlling structure 150 includes a contact member having a surface-engaging portion that is forcibly-biased into contact with the exterior surface of the mounting portion 130 of the first cleaning member control mechanism 122. The surface-engaging portion is sized and/or shaped to engage the circumferential groove 148.

Referring now to FIGS. 13-18, various aspects of an in vivo endoscope cleaning apparatus configured in accordance with a second embodiment of the present invention, which is designated as cleaning apparatus 200, are discussed. With the exception of the following distinguishing aspects of the cleaning apparatus 200, the cleaning apparatus 200 can be generally of the same configuration as the cleaning apparatus 100 discussed above in reference to FIGS. 2-12, interfaces with commercially available endoscopes and is intended for use in the same manner described above for cleaning apparatus 100. However, as will be seen, the cleaning apparatus 200 includes a cleaning member controller construction that is different in function and structure than that of cleaning apparatus 100. Similar elements in the first and second embodiments are designated by similar reference numbers and/or names (e.g., user interface body 103 and user interface body 203).

A user interface body 203 of the cleaning apparatus 200 carries a cleaning member controller 220. The following description will describe the operation of the cleaning member controller 220, which provides a cleaning member movement arrangement that is structure-mandated. In contrast, the cleaning member controller 120 of the cleaning apparatus 100 discussed above in reference to FIGS. 2-12 utilizes a cleaning member movement arrangement that is user-mandated.

Figure 13:
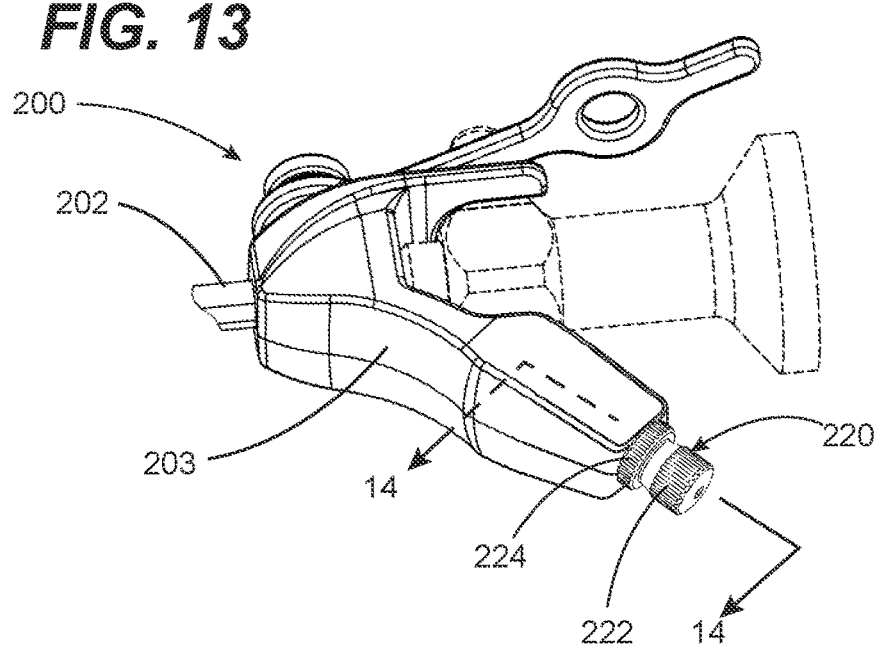
FIG. 13 is a perspective view showing an endoscope cleaning apparatus in accordance with a second embodiment of the present invention.
Figure 14:
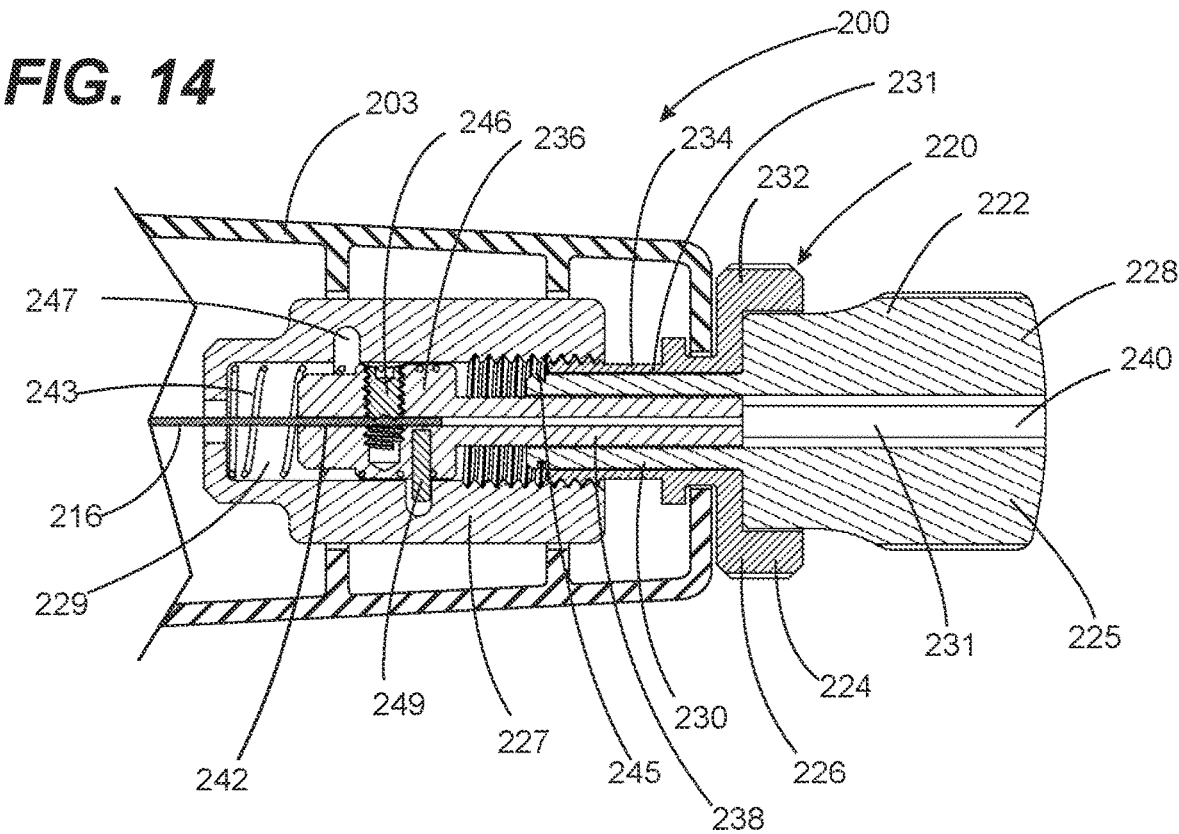
FIG. 14 is a cross-sectional view taken along the line 14-14 in FIG. 13.

The cleaning member controller 220 is coupled between the user interface body 203 and a cleaning member of the cleaning apparatus 200 for enabling selective movement of the cleaning member. (i.e., functionally and/or structurally the same as the cleaning member controller 120 of the cleaning apparatus 100 is coupled to the cleaning member 114 thereof.) The cleaning member controller 220 includes a first cleaning member control mechanism 222 and a second cleaning member control mechanism 224. The first and second cleaning member control mechanisms 222, 224 each include a respective control body 225, 226 (i.e., the first control body 225 and second control body 226) that is rotatably attached to the user interface body 203, as best shown in FIGS. 13 and 14. The first cleaning member control mechanism 222 utilizes rotational movement thereof for synchronously moving the cleaning member between a stowed position S (See FIG. 7) and a use position U (See FIG. 8) and into and away from contact with the imaging element of the endoscope 1 (See FIGS. 7-9). The first cleaning member control mechanism 222 thus provides combines the previously-mentioned first and second cleaning member manipulation modes. The second cleaning member control mechanism 224 utilizes rotational movement thereof to provide a cleaning member manipulation mode (i.e., previously referred to as the third cleaning member manipulation mode) for adjusting an axial distance between the cleaning member and an imaging element of the endoscope when the cleaning member is in the use position. In this manner, the first cleaning member manipulation mode of the first cleaning member control mechanism 222 permits manipulation of the cleaning member for enabling in vivo cleaning of the endoscope's imaging element in concert with in vivo surgical cavity visualization utilizing the imaging element.

Referring to FIGS. 14 and 15, the first cleaning member control mechanism 222 includes the first control body 225, a cam body 227 and a coupling element engaging structure 236 and the second cleaning member control mechanism 222 includes the second control body 226. The first control body 225 includes a user interface portion 228 and a mounting portion 230 connected to the user interface portion 228 thereof. The second control body 226 includes a user interface portion 232 and a mounting portion 234 connected to the user interface portion 232 thereof. Preferably, as shown, the first control body 225 is in a nested arrangement with the second control body 226.

A proximate end portion of the coupling element 216 into a coupling element passage 242 of the coupling element engaging structure 236. The coupling element engaging structure 236 includes a securement structure 246 (e.g., a threaded setscrew) for securing the coupling element 216 in a fixed placement relative to the coupling element engaging structure 236. Accordingly, as discussed below in greater detail, axial displacement of the coupling element engaging structure 236 results in a corresponding axial displacement of coupling element 216 and the cleaning member attached to the distal end portion thereof.

The coupling element engaging structure 236 is translatably and rotatably seated within a central passage 229 of the cam body 227. The mounting portion 234 of the second cleaning member control mechanism 224 (e.g., a first structural element of an interlocked interface structure) is disposed within the central passage 229 of the cam body 227 and is threadedly engaged with the cam body 227 (e.g., a second structural element of an interlocked interface structure), whereby rotation of the second control body 226 causes axial displacement of the cam body 227 relative to the mounting portion 234 of the second cleaning member control mechanism 224. The cam body 227 is mounted on the user interface body 203 and is jointly configured with the user interface body 203 to permit axial translation of the cam body 227 relative to the user interface body 203 and inhibit unrestricted rotational movement therebetween (i.e., a translation-enabling, rotation-inhibiting interface). The mounting portion 234 of the second cleaning member control mechanism 224 is engaged with user interface housing 203 to permit rotational movement of the second control body 226 relative to the user interface housing 203, while inhibiting unrestricted axial displacement therebetween (i.e., a rotation-enabling, translation-inhibiting interface). The mounting portion 230 of the first cleaning member control mechanism 222 is rotatably disposed within the central passage 229 of the cam body 227, extending through a central passage 231 of the second control body 226.

The coupling element engaging structure 236 includes an extension portion 238 that is engaged within a central passage 240 of the first control body 225. Mating surface of the extension portion 238 and the central passage 240 are jointly configured to permit relative axial translation between the extension portion 238 and the first control body 225, while inhibiting relative rotation therebetween (i.e., translation-enabling, rotation-inhibiting interface). For example, the extension portion 238 can have a non-circular cross-sectional profile (e.g., a square or star shaped cross-sectional profile) and the central passage 240 can correspondingly have a non-circular cross-sectional profile. A resilient member 243 (e.g., spring) is engaged between the cam body 227 and the coupling element engaging structure 236 for biasing the extension portion of the coupling element engaging structure 236 toward the central passage 240 of the first cleaning member control mechanism 222.

The mounting portion 230 of the first cleaning member control mechanism 222 includes a travel limiting element 245 that is fixedly attached thereto and that engages one or more surface of the mounting portion 234 of the second cleaning member control mechanism 224. For example, the travel limiting element 245 can abut an end face of the mounting portion 234 of the second cleaning member control mechanism 224, as shown, or can engaged a groove at an intermediate location of the mounting portion 234. Such engagement of the travel limiting element 245 with one or more surfaces of the second cleaning member control mechanism 224 secures the first cleaning member control mechanism 222 in axial position relative to the second cleaning member control mechanism 224 while enabling rotation movement therebetween. Such securement of the first and second cleaning member control mechanism 222, 224 and the threaded engagement of the mounting portion 234 of the second cleaning member control mechanism 224 with the cam body 227 provides for axial displacement of the cam body 227 relative to the first and second cleaning member control mechanisms 222, 224 when second control body 226 is rotated (e.g., clock-wise rotation provides axial movement in one direction and counter clock-wise rotation provides axial movement in the opposite direction).

Referring now to FIGS. 15-18, the cam body 227 includes a camming structure 247 (i.e., a cam surface providing structure) that defines an axial position of the cleaning member as a function of angular position of the first control body 225. In one or more embodiments, the camming structure 247 can be a slot (i.e., including channels and recessed portions) and the slot can extend entirely through a wall defining the central passage 229. In one or more other embodiments, the functionality of the camming structure 247 can be provided by a track or other structure that includes a profiled surface defining an axial position of the cleaning member as a function of angular position of a control portion of the cleaning member controller. A motion control member 249 (e.g., a pin) has a first end portion thereof fixedly attached to the coupling element engaging structure 236 and a second end portion thereof slidably engaged with the camming structure 247 (e.g., a pin within a slot). The camming structure 247 has a profile that at least partially defines a path of travel of the motion control member 249. Accordingly, in use, rotation of the first control body 225 causes the motion control member 249 to travel along such path and, thus provide a corresponding axial movement of the coupling element engaging structure 236 to which the cleaning member is attached through the coupling element 214.

The cam body 226, the coupling element engaging structure 236 and the motion control member 249 jointly define a motion control device. The cam body 227 includes a motion control structure that defines an axial position of the coupling element engaging structure 236 as a function of angular position of the first control body 225. The motion control device provides for rotational and axial movement of the cleaning member and thus a cleaning member attached thereto via the coupling element 216.

In one or more embodiments, as shown in FIGS. 15-18, the camming structure 247 of the cam body 227 is circumferential such that it extends around an entire circumference of the camming structure 247. The camming structure 247 has a plurality of cam segments. A first one of these cam segments (the first cam segment 252) can be a dwell segment during which the cleaning member is rotated while in a stowed position relative to a distal end portion of an elongated body 202 (FIG. 13) of the cleaning apparatus 200. A second one of these cam segments (the second cam segment 254) can be a deployment segment during which the cleaning member is deployed from the stowed position to a use position (i.e., axially displace away from the distal end portion of the elongated body 202). A third one of these cam segments (the third cam segment 256) can be a contact segment during which the cleaning member is rotated into and away from contact with the imaging element of the endoscope while the cleaning member remains fully or partially axially displaced axially away from the distal end portion of the elongated body 202 by a distance defined at least partially by the second and third cam segment 254, 256. For example, third cam segment 256 can have a slope for causing the cleaning member to exhibit a corresponding axial displacement. A fourth one of these cam segments (the fourth cam segment 258) can be a retraction segment during which the cleaning member returns to the stowed position. The resilient member provides a biasing force for urging the coupling element engaging structure 236 toward to fully retracted position and thus the cleaning member toward the stowed position.

Movement of the motion control member 249 through these cam segments defines a current instance of a cleaning cycle. A next instance of cleaning cycle 260 is initiated upon rotation of the first control body 225. The retraction segment 258 also can serve as an anti-rotation tool by, for example, the retraction segment 258 and the dwell segment 252 having a steep vertical profile (e.g., 90-degree angle therebetween) that prevents the motion control member 249 moving in an unintended direction of rotation.

In one or more other embodiment of the present invention, the second cleaning member control mechanism 224 can be omitted. Omission of the second cleaning member control mechanism 224 provides for the first control body 225 to be rotatably mounted on the chassis and enables the first control body 225 to be attached to the coupling element engaging structure 236 in a manner that inhibits both rotational movement and axial movement of the first control body 225 with respect to the coupling element engaging structure 236. Such an embodiment provides the aforementioned combined first and second control member manipulation modes while omitting the aforementioned third control member manipulation modes Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An imaging element cleaning apparatus, comprising:
   a chassis;
   a cleaning member at a distal end portion of the chassis; and
   a cleaning member movement mechanism attached to the chassis at a location spaced away from the distal end portion of the chassis, wherein the cleaning member movement mechanism includes a motion control device comprising a cleaning member coupling element and a cam body, wherein the cleaning member is coupled to the cleaning member coupling element for inhibiting unrestricted relative movement therebetween whereby movement of the cleaning member coupling element to each angular position thereof causes the cleaning member to move to a corresponding angular position thereof over an entire range of motion of the cleaning member coupling element and wherein a profile of a motion control surface of the cam body defines axial position of the cleaning member coupling element relative to the chassis as a function of angular position of the cleaning member coupling element such that the cleaning member being fixedly coupled to the cleaning member coupling element causes each particular angular position of the cleaning member coupling element to be associated with a respective spatial orientation and position of the cleaning member relative to the distal end portion of the chassis.

2. The imaging element cleaning apparatus of claim 1 wherein:
   the chassis includes a user interface body and an elongated body attached to the user interface body;
   the cam body is mounted on the user interface body to enable axial translation of the cam body along a longitudinal centerline axis thereof relative to the user interface body and to inhibit unrestricted rotational displacement of the cam body about the longitudinal centerline axis thereof relative to the user interface body; and
   a distal end portion of the elongated body is the distal end portion of the chassis.

3. The imaging element cleaning apparatus of claim 1 wherein the cleaning member coupling element has a motion control member thereof engaged with the motion control surface whereby rotation of the cleaning member coupling element results in movement of the cleaning member relative to the chassis in accordance with the profile of the motion control surface.

4. The imaging element cleaning apparatus of claim 1 wherein:
   the cleaning member movement mechanism includes a control body rotatably coupled to the chassis; and
   the cleaning member coupling element is engaged with the control body to inhibit unrestricted rotational movement therebetween over an entire range of rotation of the control body whereby rotation of the control body causes a corresponding rotation of the cleaning member coupling element over the entire range of rotation of the control body.

5. The imaging element cleaning apparatus of claim 4 wherein:
   the motion control surface is defined by a channel extending through a surface of the cam body; and
   a motion control member of the cleaning member movement mechanism is engaged within the channel.

6. The imaging element cleaning apparatus of claim 4 wherein the cleaning member coupling element has a motion control member thereof engaged with the motion control surface whereby rotation of the control body results in movement of the cleaning member relative to the chassis in accordance with the profile of the motion control surface.

7. The imaging element cleaning apparatus of claim 6 wherein:
   the motion control surface is defined by a channel extending through a surface the cam body; and
   the motion control member is engaged within the channel.

8. The imaging element cleaning apparatus of claim 1 wherein:
   the motion control surface is defined by a channel extending through a surface of the cam body; and
   the channel extends at least partially around a circumference of the cam body.

9. The imaging element cleaning apparatus of claim 8 wherein the cleaning member coupling element has a motion control member thereof engaged with the channel whereby rotation of the cleaning member coupling element results in movement of the cleaning member relative to the chassis in accordance with the profile of the motion control surface.

10. The imaging element cleaning apparatus of claim 9 wherein:
the cleaning member movement mechanism includes a control body rotatably coupled to the chassis; and
the cleaning member coupling element is engaged with the control body to inhibit unrestricted rotational movement therebetween over an entire range of rotation of the control body whereby rotation of the control body causes a corresponding rotation of the cleaning member coupling element over the entire range of rotation of the control body.

11. An imaging element cleaning apparatus, comprising:
a chassis;
a cleaning member including an imaging element wiper;
a coupling element coupled to the chassis and having a distal end thereof fixedly attached to the cleaning member; and
a cleaning member movement mechanism including a cam body, a control body and a cleaning member coupling element, wherein the control body is rotatably attached to the chassis, wherein the cleaning member coupling element is movably engaged with the cam body and has the coupling element fixedly attached thereto, wherein the cam body is engaged with the chassis and includes a motion control surface along which a motion control member of the cleaning member coupling element travels to cause axial movement of the cleaning member coupling element with respect to the cam body as a function of angular position of the cleaning member coupling element and wherein the control body is attached to the cleaning member coupling element to inhibit unrestricted rotational movement therebetween over an entire range of rotation of the control body.

12. The imaging element cleaning apparatus of claim 11 wherein:
the chassis includes a user interface body and an elongated body attached to the user interface body;
the cam body is mounted on the user interface body to enable axial translation of the cam body along a longitudinal centerline axis thereof relative to the user interface body and to inhibit unrestricted rotational displacement of the cam body about the longitudinal centerline axis thereof relative to the user interface body; and
the cleaning member is spaced away from a distal end portion of the elongated body.

13. The imaging element cleaning apparatus of claim 11 wherein said engagement of the control body to the cleaning member coupling element enables axial translation of the cleaning member coupling element relative to the control body.

14. The imaging element cleaning apparatus of claim 13 wherein the control body is coupled to a control body mounting portion of the chassis that inhibits unrestricted axial displacement of the control body relative to the chassis.

15. The imaging element cleaning apparatus of claim 14 wherein:
the chassis includes a user interface body and an elongated body attached to the user interface body;
the cam body is mounted on the user interface body to enable axial translation of the cam body along a longitudinal centerline axis thereof relative to the user interface body and to inhibit unrestricted rotational displacement of the cam body about the longitudinal centerline axis thereof relative to the user interface body; and
the cleaning member is spaced away from a distal end portion of the elongated body.

16. The imaging element cleaning apparatus of claim 13 wherein:
the motion control surface is defined by a channel within the cam body; and
the motion control member is engaged within the channel.

17. The imaging element cleaning apparatus of claim 16 wherein a coupling element engaging structure of the cleaning member coupling element is located within a central passage of the cam body.

18. An imaging element cleaning apparatus, comprising:
a chassis;
a cleaning member;
a cleaning member coupling element attached at a distal end portion thereof to the cleaning member;
a control body rotatably attached to the chassis and attached to a proximate end portion of the cleaning member coupling element to inhibit unrestricted rotational movement therebetween over an entire range of rotation of the control body whereby rotation of the control body to causes a corresponding rotational movement of the cleaning member coupling element over the entire range of rotation of the control body; and
a cam body including a motion control surface having a profile that defines axial movement of the cleaning member coupling element with respect to the cam body as a function of angular position of the control body, wherein the cleaning member coupling element is engaged with the cam body and wherein the cleaning member coupling element has a motion coupling element thereof engaged with the motion control surface whereby rotation of the control body results in movement of the cleaning member relative to the cam body in accordance with the profile of the motion control surface.

19. The imaging element cleaning apparatus of claim 18 wherein:
the chassis includes a user interface body and an elongated body attached to the user interface body; and
the cam body is mounted on the user interface body to enable axial translation of the cam body along a longitudinal centerline axis thereof relative to the user interface body and to inhibit unrestricted rotational displacement of the cam body about the longitudinal centerline axis thereof relative to the user interface body.

20. The imaging element cleaning apparatus of claim 18 wherein said attachment of the control body to the cleaning member coupling element enables axial translation of the cleaning member coupling element relative to the control body.

21. The imaging element cleaning apparatus of claim 20 wherein the control body is coupled to a control body mounting portion of the chassis to inhibit unrestricted axial displacement of the control body relative to the chassis.

22. The imaging element cleaning apparatus of claim 21 wherein:

the chassis includes a user interface body and an elongated body attached to the user interface body; and the cam body is mounted on the user interface body to enable axial translation of the cam body along a longitudinal centerline axis thereof relative to the user interface body and to inhibit unrestricted rotational displacement of the cam body about the longitudinal centerline axis thereof relative to the user interface body.

23. The imaging element cleaning apparatus of claim 18 wherein:

the motion control surface is defined by a channel within the cam body; and the motion control member is engaged within the channel.

24. The imaging element cleaning apparatus of claim 23 wherein:

a coupling element engaging structure of the cleaning member coupling element is located within a central passage of the cam body;

said attachment of the control body to the cleaning member coupling element permits axial displacement therebetween; and the control body is coupled to a control body mounting portion of the chassis to inhibit unrestricted axial displacement of the control body relative to the chassis.

* * * * *